United States Patent [19]

Riondel et al.

[11] Patent Number: 5,610,313

[45] Date of Patent: Mar. 11, 1997

[54] PROCESS FOR THE PREPARATION OF ALKYLIMIDAZOLIDONE (METH) ACRYLATES

[75] Inventors: Alain Riondel, Forbach; Gilles Herbst, Spicheren; André Levray, Saint Avold, all of France

[73] Assignee: ELF Atochem S.A., Puteaux, France

[21] Appl. No.: 544,438

[22] Filed: Nov. 17, 1995

[30] Foreign Application Priority Data

Nov. 18, 1994 [FR] France .................... 94 13848

[51] Int. Cl.$^6$ ................................ C07D 233/32
[52] U.S. Cl. ................ 548/324.1; 540/460; 540/492; 544/318
[58] Field of Search .......................... 548/324.1

[56] References Cited

U.S. PATENT DOCUMENTS

| | | | |
|---|---|---|---|
| 4,777,265 | 10/1988 | Merger et al. | 548/324.1 |
| 5,210,199 | 5/1993 | Grosius et al. | 548/324.1 |
| 5,498,723 | 3/1996 | Riondel et al. | 548/324.1 |

FOREIGN PATENT DOCUMENTS

| | | |
|---|---|---|
| 0236994 | 9/1987 | European Pat. Off. . |
| 0433135 | 6/1991 | European Pat. Off. . |
| 0453638 | 10/1991 | European Pat. Off. . |
| 0571851 | 12/1993 | European Pat. Off. . |
| 0619309 | 10/1994 | European Pat. Off. . |
| 0650962 | 5/1995 | European Pat. Off. . |

Primary Examiner—Fiona T. Powers
Attorney, Agent, or Firm—Millen, White, Zelano & Branigan, P.C.

[57] ABSTRACT

A compound (I) is prepared by reacting at least one (meth) acrylate (II) with a heterocyclic alcohol (III), in the presence of a catalyst consisting of a mixture formed (a) of at least one magnesium alkoxide and (b) of a component chosen from the chelates of calcium with 1,3-dicarbonyl compounds, dialkyltin oxides, dialkyltin alkoxides and dialkyltin diesters.

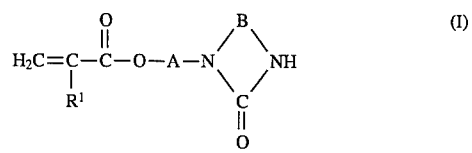

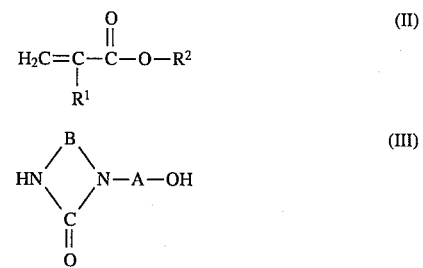

$R = C_1-C_4$ alkyl.
$R^1 = H, CH_3$; A, B = straight or branched $C_2-C_5$ hydrocarbon chain; $R^2 = C_1-C_4$ alkyl.

15 Claims, No Drawings

PROCESS FOR THE PREPARATION OF ALKYLIMIDAZOLIDONE (METH) ACRYLATES

The present invention relates to a process for the manufacture of a compound of formula:

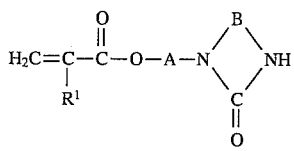

in which:

$R^1$ represents hydrogen or methyl; and

A and B each independently represent a straight or branched hydrocarbon chain having from 2 to 5 carbon atoms, by reaction of at least one (meth)acrylate of formula:

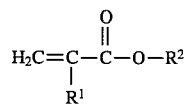

in which:

$R^1$ has the abovementioned meaning; and $R^2$ represents a $C_1$–$C_4$ alkyl group, with a heterocyclic alcohol of formula:

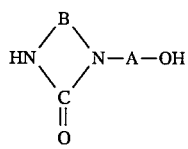

in which A and B have the abovementioned meanings.

These compounds of formula (I) are known for their role in making up polymers which are useful as coatings and adhesives, for the treatment of paper and textiles, in particular from American patent U.S. Pat. No. 2,871,223, as well as for their uses as leather-treating agents, and in the production of emulsion paints. Ethylimidazolidone methacrylate (EIOM) is mainly used in paints as a promoter of wet adhesion.

It is known from European patent application EP-A-0,433,135 that it is possible to use, as catalysts for this reaction, dialkyltin oxides, dialkyltin dialkoxides and dialkyltin diesters. Di-n-butyltin oxide (DBTO) are mentioned, inter alia.

However, in the case of the synthesis of EIOM, it is desirable to achieve the most complete conversion possible of the hydroxyethylimidazolidone (HEIO), which, in the case of catalysis by DBTO, requires a high level of temperature.

Another catalyst has therefore been sought which would make it possible in particular to obtain a normal level of production efficiency at lower reaction temperatures.

The Applicant Company thus discovered that the use of a chelate of calcium with a 1,3-dicarbonyl compound, in particular calcium acetylacetonate (Ca(acac)$_2$), or of such a chelate mixed with at least one from among dialkyltin oxides, dialkyltin dialkoxides and dialkyltin esters, makes it possible to perform the process at a temperature below 100° C. (95° C.–96° C. in particular), while at the same time leading to comparable results from the point of view of the yield of EIOM and of the conversion of HEIO. This has formed the subject of French patent application FR-A-2,703,682.

The Applicant Company simultaneously discovered that the use of a magnesium alkoxide makes it possible to achieve the same results (French patent application No. 93/12833 of 27 Oct. 1993).

During its endeavors to enhance further the catalytic activity, the Applicant Company has now discovered that the combination of a magnesium alkoxide with another catalyst chosen from the abovementioned calcium chelates and the abovementioned tin compounds, allows catalysis with much faster kinetics than those observed in the best of the cases with the magnesium alkoxide alone.

The subject of the present invention is thus a process for the manufacture of a compound of formula (I), as has been defined above, in the presence of a catalyst consisting of a mixture formed (a) of at least one magnesium alkoxide and (b) of a component chosen from the chelates of calcium with 1,3-dicarbonyl compounds, dialkyltin oxides, dialkyltin alkoxides and diaikyltin diesters.

By way of examples of magnesium alkoxides Mg(OR)$_2$, there may be mentioned those in which R represents a linear $C_1$–$C_4$ alkyl group, such as methyl, ethyl, n-propyl or n-butyl. The alkoxides in which R represents ethyl or n-propyl may be mentioned more particularly.

It is preferred to use magnesium diethoxide as constituent (a) of the useful catalyst according to the invention.

By way of examples of dicarbonyl compounds, there may be mentioned a β-keto acid ester, such as the acetylacetic ester, or a 1,3-diketone, such as acetylacetone, 3-methylacetylacetone, benzoylacetone, dibenzoylmethane, 2,4-hexanedione, 3,5-heptanedione, 3-phenylacetylacetone, 4,4,4-trifluoro-1-phenyl-1,3-butanedione, 2,2,6,6-tetramethyl-3,5-heptanedione, 1,1,1-trifluoro-5,5-dimethyl -2,4-hexanedione and 1,1,1-trifluoro-2,4-pentanedione. In particular, calcium acetylacetonate may be mentioned as component (b) of the useful catalyst according to the invention.

Di-n-butyltin oxide (DBTO) is mentioned in particular as a dialkyltin oxide falling within the definition of the constituent (b) of the catalyst.

Methyl, ethyl, n-propyl, n-butyl and isobutyl acrylates and methacrylates may be mentioned in particular as examples of reactants of formula (II).

1-(2-Hydroxyethyl)-2-imidazolidone (HEIO) may be mentioned in particular as an example of a heterocyclic alcohol of formula (III).

In order to carry out the process according to the invention, the constituent (a) of the catalyst is used in an amount generally of between 0.5 and 4 mol % approximately and, preferably, between 1 and 2.5 mol % approximately, and the constituent (b) is used in an amount generally of between 0.01 and 2 mol % approximately and, preferably, of between 0.02 and 1 mol % approximately, the amounts being given relative to the heterocyclic alcohol of formula (III).

The reaction of the process according to the invention may be carried out in the presence of an excess of one or other of the reactants. It is, however, advisable for the molar ratio of the (meth)acrylate of formula (II) to the heterocyclic alcohol of formula (III) to be approximately between 1.1 and 7.0, preferably between 2.0 and 6.0. By working with a large molar excess of (meth)acrylate relative to the heterocyclic alcohol, a solution of compound of formula (I) in the (meth)acrylate is obtained at the end of the reaction, which solution may be used directly for certain applications, such as for the production of paints and coatings, or alternatively for the treatment of leather.

The reaction of the process according to the invention is preferably carried out in the presence of at least one polymerization inhibitor, which is used, for example, in a proportion of from 0.05 to 0.5% by weight based on the weight of the heterocyclic alcohol of formula (III). Phenothiazine, hydroquinone methyl ether, di-tert-butylcatechol, hydroquinone, p-anilinophenol, para-phenylenediamine, and mixtures thereof in all proportions, may be mentioned in particular as examples of polymerization inhibitors which may be used.

The reaction of the process according to the invention is preferably carried out at a pressure which does not exceed atmospheric pressure, for example at a pressure of between 0.3 and 1 bar. The reaction is advantageously performed under an air sparge in order to enhance the effectiveness of the stabilizers. It is carried out by mixing the (meth)acrylate of formula (II) and the heterocyclic alcohol of formula (III), and heating the reaction mixture to reflux, generally to a temperature of between 75° and 105° C., this temperature obviously being dependent on the exact nature of the alcohol and of the (meth)acrylate, and on the catalytic system used.

When carrying out the process according to the invention, it is recommended to achieve maximum dehydration before addition of the catalyst, so as to avoid its deactivation by water. It is possible to arrive at this result, for example, by heating the initial mixture of (meth)acrylate of formula (II), heterocyclic alcohol of formula (III) and polymerization inhibitor to reflux, while at the same time separating out by distillation the azeotrope of (meth)acrylate and water when a methacrylate and water azeotrope forms. At this stage, after separation of the distillate, the catalyst is introduced into the hot reaction mixture.

The duration of the reaction according to the invention obviously depends upon the reaction conditions, such as the temperature, the pressure and the amount of catalyst used, but is generally approximately between 3 and 15 hours. It obviously also depends upon the nature of the reactants used.

The reaction mixture is thus heated to reflux until the head temperature reaches the temperature of distillation of the azeotrope of the (meth)acrylate and the alcohol of formula $R_2OH$ formed by the reaction, when an azeotrope forms.

Any excess (meth)acrylate may then be removed by evaporation, so as to isolate the compound of formula (I) from the reaction medium, generally in the solid state: thus, 1-(2-hydroxyethyl)-2-imidazolidone acrylate is a white crystalline solid with a melting point equal to 43° C., which is soluble under cold conditions in ketones, alcohols, aromatic hydrocarbons and water, insoluble under cold conditions in saturated hydrocarbons and precipitates at 0° C. from ethyl acrylate. 1-(2-Hydroxyethyl)-2-imidazolidone methacrylate is a white crystalline solid with a melting point equal to 47° C., having the same solubility properties as the above acrylate. After the evaporation operation, the solid crystalline product may in addition be purified by filtration, followed by washing with petroleum ether and drying.

The compound (I) may also be isolated by partial evaporation of the (meth) acrylate, followed by crystallization at a sufficiently low temperature (preferably below or equal to 0° C.) and for a sufficiently long period (which may be up to 15 hours) and then by filtration, followed by the purification steps described above.

Finally, a third method for isolating the compound of formula (I) from the solution containing it consists in carrying out an extraction with water, followed by a separation after settling, a concentration of the (meth)acrylate, and the purification steps described above.

The examples which follow illustrate the invention without, however, limiting it. In these examples, the percentages are given by weight except where otherwise mentioned.

EXAMPLES 1 AND 2 (COMPARATIVE), 3 (OF THE INVENTION), 4 (COMPARATIVE) AND 5 (OF THE INVENTION)

General procedure:

221 g of HEIO and 635 g of methyl methacrylate (MAM), along with 0.4 g of phenothiazine (PTZ) as stabilizer, are introduced into a jacketed glass reactor equipped with a temperature-measuring probe, a variable-speed mechanical stirrer and a packed adiabatic column on which is mounted a reflux head. Stabilization at the column head is established by a 0.1% solution of hydroquinone methyl ether (HQME) in MAM. The contents of the reactor are maintained at boiling under atmospheric pressure for 1 hour, at a column head temperature of 98°–100° C. and at a temperature at the foot of the column of below or equal to 100° C., and the water is removed by azeotropic distillation with methyl methacrylate.

Next, the catalyst or catalysts are introduced into the reactor using the amount indicated, along with the amount of MAM necessary to obtain an MAM/HEIO molar ratio equal to 3.5. The pressure is adjusted in order to maintain a temperature of 95° C. in the reactor. The withdrawal of the MAM/MeOH azeotrope is controlled by a set temperature at the column head (equal to 63° C.). When the amount of methanol withdrawn corresponds to the expected amount, the reaction is continued until no further formation of methanol is observed (column head temperature=boiling point of the MAM), at full reflux, and at the pressure considered.

After cooling, crude EIOM is recovered.

The yield of EIOM and the conversion of the HEIO are determined by liquid phase chromatography (HPLC) of the crude reaction product, via the following equations:

$$\text{HEIO conversion } C\,(\%) = \frac{(\text{Starting HEIO} - \text{final HEIO})}{\text{Starting HEIO}} \times 100$$

$$\text{EIOM Yield } Y\,(\%) = \frac{\text{Number of moles of EIOM formed}}{\text{Number of moles of starting HEIO}} \times 100$$

The results of the various tests carried out are given in Tables 1 and 2 below. The conversion C of the HEIO and the yield Y of the EIOM are given in these tables.

TABLE 1

| Example | Catalyst and molar % of catalyst relative to HEIO | Duration (h) | HPLC analysis of the crude mixture obtained (5) | | | C (%) | Y (%) |
|---|---|---|---|---|---|---|---|
| | | | MAM | HEIO | EIOM | | |
| 1 (comparative) | $(EtO)_2Mg$ (2) | 7 | 47.4 | 0.3 | 42.5 | 99.2 | 73 |
| 2 (comparative) | DBTO (0.23) | 6 | 60.1 | 11.7 | 23.4 | 59.2 | 53.4 |
| 3 | $(EtO)_2Mg$ (2) + DBTO (0.23) | 5.5 | 49 | 0.84 | 39.5 | 95.5 | 81 |
| 4 (comparative) | $Ca(acac)_2$ (0.04) | 6 | 55.8 | 10.3 | 31.2 | 69.9 | 59.9 |
| 5 | $(EtO)_2Mg$ (2) + $Ca(acac)_2$ (0.04) | 4.5 | 30.5 | 1.1 | 53.3 | 97.6 | 75 |

TABLE 2

| Catalyst and molar % of catalyst relative to HEIO | C (%) | | | |
|---|---|---|---|---|
| | 1 h | 2 h | 3 h | 4 h |
| $(EtO)_2Mg$ (2) | | 31 | 43 | 63 |
| DBTO (0.23) | | 21 | 23 | 26 |
| $(EtO)_2Mg$ (2) + DBTO (0.23) | | 52 (calculated) / 62 | 66 (calculated) / 89 | 89 (calculated) / 100 |
| $(EtO)_2Mg$ (2) | 14 | 32 | 43 | 43 |
| $Ca(acac)_2$ (0.04) | 18 | 32 | 43 | 43 |
| $(EtO)_2Mg$ (2) + $Ca(acac)_2$ (0.04) | 32 (calculated) / 75 | 64 (calculated) / 85 | 86 (calculated) / 95 | |

C (%): Conversion as a function of time

The results given in Table 1 show a catalytic activity for the two-component systems of Examples 3 and 5 which is higher than that of the catalytic components taken separately.

This high activity is reflected in a significant decrease in the reaction time. It does not result from a simple addition of the catalytic performances of the individual components of these systems, in terms of conversion of the HEIO, but from a synergism between the said individual components, for when the results of Table 2 are examined, it is seen that the theoretical conversion of the HEIO during the first four hours of the reaction, resulting from the calculated addition of the conversions obtained with each individual catalytic component, is less than that given by the catalytic systems of the invention.

We claim:

1. Process for the manufacture of a compound of formula:

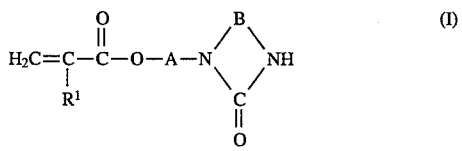

(I)

in which:

$R^1$ represents hydrogen or methyl; and

A and B each independently represent a straight or branched hydrocarbon chain having from 2 to 5 carbon atoms, by reaction of at least one (meth)acrylate of formula:

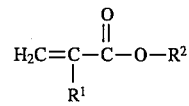

(II)

in which:

$R^1$ has the abovementioned meaning; and $R^2$ represents a $C_1$–$C_4$ alkyl group, with a heterocyclic alcohol of formula:

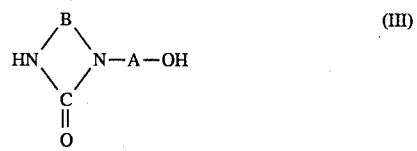

(III)

in which A and B have the abovementioned meanings, in the presence of a catalyst consisting essentially of a mixture formed (a) of at least one magnesium alkoxide and (b) of a component chosen from the chelates of calcium with 1,3-dicarbonyl compounds, dialkyltin oxides, dialkyltin alkoxides and dialkyltin diesters.

2. Process according to claim 1, characterized in that a magnesium alkoxide $Mg(OR)_2$, R representing a $C_1$–$C_4$ alkyl residue, is used as constituent (a) of the catalyst.

3. Process according to claim 2, characterized in that R represents ethyl or n-propyl.

4. Process according to claim 3, characterized in that calcium acetylacetonate is used as calcium chelate.

5. Process according to claim 4, characterized in that di-n-butyltin oxide is chosen as constituent (b) of the catalyst.

6. Process according to claim 1, characterized in that a chelate of calcium with a β-keto acid ester or with a 1,3-diketone is chosen as constituent (b) of the catalyst.

7. Process according to claim 6, characterized in that calcium acetylacetonate is used as calcium chelate.

8. Process according to claim 6 wherein the β-keto acid ester is acetylacetic ester.

9. Process according to claim 6 wherein the 1,3-diketone is acetylacetone, 3-methylacetylacetone, benzoylacetone, dibenzoylmethane, 2,4-hexanedione, 3,5-heptanedione, 3-phenylacetylacetone, 4,4,4-trifluoro-1-phenyl-1,3-butanedione, 2,2,6,6-tetramethyl-3,5-heptanedione, 1,1,1-trifluoro-5,5-dimethyl-2,4-hexanedione or 1,1,1-trifluoro-2,4-pentanedione.

10. Process according to claim 1, characterized in that di-n-butyltin oxide is chosen as constituent (b) of the catalyst.

11. Process according to claim 1, characterized in that the constituent (a) of the catalyst is used in an amount of from 0.5 to 4 mol % and the constituent (b) is used in an amount of from 0.01 to 2 mol %, these amounts being given relative to the heterocyclic alcohol of formula (III).

12. Process according to claim 1, characterized in that the reaction is performed at a temperature of between 75° and 105° C.

13. Process according to claim 1, characterized in that a molar ratio of the (meth)acrylate of formula (II) to the heterocyclic alcohol of formula (III) which is between 1.1 and 7.0 is used.

14. Process according to claim 1, characterized in that the reaction is performed for a period of between 3 and 15 hours, at a pressure which does not exceed atmospheric pressure.

15. Process according to claim 1, characterized in that the reaction is performed in the presence of at least one polymerization inhibitor chosen from phenothiazine, hydroquinone methyl ether, di-tert-butylcatechol, hydroquinone, p-anilinophenol, para-phenylenediamine, and mixtures thereof in all proportions.

* * * * *